United States Patent
Kamata et al.

(10) Patent No.: US 9,908,104 B2
(45) Date of Patent: Mar. 6, 2018

(54) METHANATION CATALYST

(71) Applicants: Agency for Science, Technology and Research, Singapore (SG); IHI Corporation, Tokyo (JP)

(72) Inventors: Hiroyuki Kamata, Tokyo (JP); Luwei Chen, Jurong Island (SG); Armando Borgna, Jurong Island (SG); Yoshinori Izumi, Tokyo (JP); Jie Chang, Jurong Island (SG); Catherine Kai Shin Choong, Jurong Island (SG)

(73) Assignees: AGENCY FOR SCIENCE, TECHNOLOGY AND RESEARCH, Singapore (SG); IHI CORPORATION, Tokyo (JP)

( * ) Notice: Subject to any disclaimer, the term of this patent is extended or adjusted under 35 U.S.C. 154(b) by 0 days.

(21) Appl. No.: 14/901,523

(22) PCT Filed: Jun. 27, 2014

(86) PCT No.: PCT/SG2014/000311
§ 371 (c)(1),
(2) Date: Dec. 28, 2015

(87) PCT Pub. No.: WO2014/209237
PCT Pub. Date: Dec. 31, 2014

(65) Prior Publication Data
US 2016/0151765 A1    Jun. 2, 2016

(30) Foreign Application Priority Data
Jun. 28, 2013 (SG) ............... 201305087-7

(51) Int. Cl.
*C07C 1/04* (2006.01)
*B01J 23/83* (2006.01)
(Continued)

(52) U.S. Cl.
CPC ............. *B01J 23/83* (2013.01); *B01J 23/002* (2013.01); *B01J 23/63* (2013.01); *B01J 35/002* (2013.01);
(Continued)

(58) Field of Classification Search
CPC . B01J 23/002; B01J 23/63; B01J 23/83; B01J 35/0013; B01J 35/002;
(Continued)

(56) References Cited

U.S. PATENT DOCUMENTS 3,962,140 A    6/1976 Alcorn et al.
4,002,658 A    1/1977 Dalla Betta et al.
(Continued)

FOREIGN PATENT DOCUMENTS

CN    101549296 A    10/2009
CN    101607198 A    12/2009
(Continued)

OTHER PUBLICATIONS

Zyryanova, M. M. et al. Chem. Eng. J. 2011, 176-17, pp. 106-103.*
(Continued)

*Primary Examiner* — Medhanit Bahta
(74) *Attorney, Agent, or Firm* — Choate, Hall & Stewart, LLP

(57) ABSTRACT

The invention relates to a catalyst, comprising a catalytic element disposed on a substrate, wherein said substrate has formula $Ce_{1-x}M_xO_2$, wherein x is between about 0 and about 0.3, optionally between about 0.01 and about 0.3, and wherein M, if present, is a metallic element other than Ce, when used for catalysing a methanation reaction. There is also described use of the catalyst for catalysing a methanation reaction and a method for methanation of a feedstock including carbon monoxide and hydrogen, said method comprising contacting the feedstock with the catalyst.

16 Claims, 3 Drawing Sheets

(51) Int. Cl.
| | | |
|---|---|---|
| B01J 23/00 | (2006.01) | |
| B01J 23/63 | (2006.01) | |
| B01J 35/00 | (2006.01) | |
| B01J 35/10 | (2006.01) | |
| B01J 37/02 | (2006.01) | |
| C10G 2/00 | (2006.01) | |
| C10L 3/08 | (2006.01) | |
| B01J 37/20 | (2006.01) | |

(52) U.S. Cl.
CPC ....... *B01J 35/0013* (2013.01); *B01J 35/1014* (2013.01); *B01J 35/1019* (2013.01); *B01J 37/0201* (2013.01); *B01J 37/0215* (2013.01); *C07C 1/044* (2013.01); *C07C 1/0435* (2013.01); *C10G 2/33* (2013.01); *C10G 2/332* (2013.01); *C10G 2/333* (2013.01); *C10L 3/08* (2013.01); *B01J 35/006* (2013.01); *B01J 35/0053* (2013.01); *B01J 35/0066* (2013.01); *B01J 37/20* (2013.01); *B01J 2523/00* (2013.01); *C07C 1/043* (2013.01); *C07C 1/0425* (2013.01); *C07C 2523/83* (2013.01); *Y02P 20/142* (2015.11)

(58) Field of Classification Search
CPC ................ B01J 35/1014; B01J 35/1019; B01J 37/0201; B01J 37/0215; B01J 2523/00; B01J 35/0053; B01J 35/006; B01J 35/0066; C07C 1/0435; C10G 2/33; C10G 2/332; C10G 2/333; C10L 3/08
See application file for complete search history.

(56) References Cited

U.S. PATENT DOCUMENTS

| | | | |
|---|---|---|---|
| 4,071,473 | A | 1/1978 | Atkinson et al. |
| 4,540,714 | A | 9/1985 | Pedersen et al. |
| 4,801,620 | A | 1/1989 | Fujitani et al. |
| 4,833,112 | A | 5/1989 | Przydrozny et al. |
| 4,906,448 | A | 3/1990 | Sauvion et al. |
| 5,500,307 | A | 3/1996 | Anzai et al. |
| 5,693,299 | A | 12/1997 | Chopin et al. |
| 2007/0249496 | A1 | 10/2007 | Wagner et al. |
| 2009/0232728 | A1 | 9/2009 | Wagner et al. |
| 2009/0288401 | A1 | 11/2009 | Kaneshiro et al. |
| 2010/0279194 | A1 | 11/2010 | Elangovan et al. |
| 2015/0246347 | A1 | 9/2015 | Miyao et al. |
| 2016/0052837 | A1 | 2/2016 | Chen et al. |

FOREIGN PATENT DOCUMENTS

| | | |
|---|---|---|
| CN | 101607199 A | 12/2009 |
| CN | 101703933 A | 5/2010 |
| CN | 102039126 A | 5/2011 |
| CN | 102949998 A | 3/2013 |
| CN | 102950006 A | 3/2013 |
| GB | 2077613 A | 12/1981 |
| JP | S5357194 A | 5/1978 |
| JP | S54-119385 A | 9/1979 |
| JP | S5692826 A | 7/1981 |
| JP | S57-15834 A | 1/1982 |
| JP | S61-161228 A | 7/1986 |
| JP | S62-061640 A | 3/1987 |
| JP | H06-140048 A | 5/1994 |
| JP | H06-226094 A | 8/1994 |
| JP | 2000-126596 A | 5/2000 |
| JP | 2001058130 A | 3/2001 |
| JP | 2004-244246 A | 9/2004 |
| JP | 2007-054713 A | 3/2007 |
| JP | 2007-196206 A | 8/2007 |
| JP | 2008136951 A | 6/2008 |
| JP | 2009-131835 A | 6/2009 |
| JP | 2011-206770 A | 10/2011 |
| JP | 2012-250143 A | 12/2012 |
| JP | 2013017913 A | 1/2013 |
| SG | 2013050877 A | 1/2015 |
| WO | WO-86/07350 A1 | 12/1986 |
| WO | WO-2010/006386 A2 | 1/2010 |
| WO | WO-2010/143783 A2 | 12/2010 |
| WO | WO-2014/038426 A1 | 3/2014 |
| WO | WO-2014/209237 A1 | 12/2014 |

OTHER PUBLICATIONS

Razzaq, R. et al. "Catalytic Methanation of CO and CO2 in Coke Oven Gas over Ni—Co/ZrO2—CeO2" Ind. Eng. Chem. Res. 2013, 52, pp. 2247-2256; Published Jan. 22, 2013.*
Wang, H. et al. "Catalytic methanol decomposition to carbon monoxide and hydrogen over Pd/CeO2—ZrO2—La2O3 with different Ce/Zr molar ratios" J. Nat. Gas Chem. 2009, 18, pp. 211-216.*
Postole, G. et al. "Catalytic Steam Methane Reforming Over Ir/Ce0.9Gd0.1O2—x: Resistance to Coke Formation and Sulfur Poisoning" Fuel Cells 2012, 12, 275-287; Abstract only.*
Demri, B. and Muster, D., XPS study of some calcium compounds, Journal of Materials Processing Technology, 55:311-314 (1995).
International Search Report for PCT/SG2014/000311, 4 pages (dated Oct. 7, 2014).
Kempegowda, R. et al., High temperature desulfurization over nano-scale high surface area ceria for application in SOFC, Korean J. Chem. Eng., 25(2):223-230 (2008).
Ma, Y. et al., A sulfur-tolerant Pd/CeO$_2$ catalyst for methanol synthesis from syngas, Journal of Natural Gas Chemistry, 17:387-390 (2008).
Ma, Y. et al., Methanol synthesis from sulfur-containing syngas over Pd/CeO$_2$ catalyst, Applied Catalysis B: Environmental, 90:99-104 (2009).
Rostrup-Nielsen, J., Chemisorption of Hydrogen Sulfide on a Supported Nickel Catalyst, Journal of Catalysis, 11:220-227 (1968).
Written Opinion for PCT/SG2014/000311, 9 pages (dated Oct. 7, 2014).
Shi, P. et al., Characterization of Silica Support Nickel Catalyst for Methanation with Improved Activity by Room Temperature Plasma Treatment, Cat. Lett., 133: 112-118 (2009).
Sigma-Alrich, Si02 powder, p. 1-3 (2016).
Xia, L. et al., Effect of Supports on Catalytic Performance of Nickel-Based Catalyst for Methanation, Chinese J. Catal., 32: 1400-1404 (2011), Original and English Translation.
Harada, T. et al., Dai 105 Kai CatSJ Meeting Toronkai A Yokoshu, 133 (Mar. 24, 2010).
Misaka, T. et al., Dai 106 Kai CatSJ Meeting Toronkai A Yokoshu, 74 (Sep. 15, 2010).
Reucroft, P.J. and Park, J.W., Reducibility and Surface Area of Coprecipitated Supported Nickel Methanation Catalysts, J. Mat. Energy Systems, 2:28-33 (1980).
Che, M. et al., Nucleation and Particle Growth Processes Involved in the Preparation of Silica-Supported Nickel Materials by a Two-step Procedure, Journal of American Chemical Society, 117(7): 2008-2018 (1995).
Database Registry, STN Accession No. 1997:427820, Chemical Abstracts Services, entered STN on Jul. 10, 1997 & Persson, A. et al., A molecular approach for nanophase metal oxide catalysts, Ceramic Transactions (Catalyst Materials for High-Temperature Processes), 73:85-92.
Ikeue, K. et al., Catalytic soot oxidation by Ag/BaCeO3 having tolerance to SO2 poisoning, Journal of the Ceramic Society, 17(11):1153-1157 (2009).
Liu, J. et al., Different valent ions-doped cerium oxides and their catalytic performances for soot oxidation, Catalysis Today, 175(1):117-123 (2011).
Schubert, S.K. et al., Comparison of the performances of single cell solid oxide fuel cell stacks with Ni8YSZ and Ni10CGO anodes with H2S containing fuel, Journal of Power Sources, 217:364-372 (2012).

(56) References Cited

OTHER PUBLICATIONS

Zheng, L.L. et al., Effect of Pd-impregnation on performance, sulfur poisoning and tolerance of Ni/GDC anode of solid oxide fuel cells, International Journal of Hydrogen Energy, 37(13):10299-10310 (2012).

* cited by examiner

METHANATION CATALYST

INCORPORATION BY CROSS REFERENCE

The present patent application is a U.S. National Stage entry of International Application No. PCT/SG2014/000311, entitled "Methanation Catalyst", filed on Jun. 27, 2014, which claims the benefit of priority from Singapore patent application SG 201305087-7, filed on Jun. 28, 2013 the entire contents of each of which are hereby incorporated by reference in their entirety herein.

FIELD

The present invention relates generally to the field of catalysis. More specifically, the present invention relates to catalysis of methanation reactions.

BACKGROUND

The use of Substitute Natural Gas (SNG) was proposed during the energy crisis in the 1970s. Today, SNG is becoming important as SNG production may potentially mitigate greenhouse gas emissions and enhance the diversity of energy and chemical resources. Combining gasification and catalytic methanation technologies may enable production of SNG from a variety of feedstocks such as coal, biomass and waste.

Currently, several commercial SNG plants are being built worldwide. In particular, coal-to-SNG technologies are becoming the new focus in China's coal-based chemical industry. For example, about 15 coal-to-SNG projects are being considered in China. It is estimated that China will have around 20 billion $Nm^3/a$ SNG capacity in 2015.

A simplified SNG production process is as follows: Feedstock, i.e., coal and biomass→Gasification→Gas cleaning and conditioning→Fuel upgrading.

One of the steps in commercial SNG production is methanation, which is a reaction that generates methane from a mixture of gases, for example, those derived from gasification of coal, biomass and waste. There is thus a need for catalysts robust enough for use in catalysing methanation reactions and which ensure a high methane yield. As sulfur poisoning of catalyst surfaces represents a major challenge in the field of catalysis, and of methanation catalysis more particularly, there is also a need for catalysts having good chemical and physical stabilities including resistance to sulfur poisoning. Further, there is a need for catalysts having improved coking resistance, as coke deposition on catalyst surfaces can lead to a drop in catalytic activity and selectivity.

It is an object of the invention to at least partially satisfy the above needs.

SUMMARY OF INVENTION

The present inventors have identified that catalysts comprising a catalytic element, for example, metallic nickel, disposed on a ceria-based substrate lead to a significant improvement in catalytic performance when used to catalyse the methanation reaction of a feedstock, and in particular, a feedstock including sulfur, when compared with conventional catalysts.

Accordingly, in a first aspect, the present invention provides a catalyst, comprising a catalytic element disposed on a substrate, wherein said substrate has formula $Ce_{1-x}M_xO_2$, wherein x is between about 0 and about 0.3, optionally between about 0.01 and about 0.3, and wherein M, if present, is a metallic element other than Ce, when used for catalysing a methanation reaction.

The following options may be used in conjunction with the first aspect either individually or in any suitable combination.

The catalytic element may be a metal. The metal may be a transition metal, e.g., it may be selected from the group consisting of Co, Fe, Pt, Ru, Rh, Pd, Ni and Ir. Therefore, the catalytic element may be Co, Fe, Pt, Ru, Rh, Pd, Ni or Ir. In particular, the catalytic element may be metallic, e.g., it may be metallic nickel, or may be metallic cobalt, or metallic palladium, or metallic platinum, or metallic iron, or metallic rhodium, or metallic ruthenium, or metallic iridium. In some instances it may be a mixture or alloy of any two or more of these metals, or may be a mixture or alloy of any one of these metals with some other metal.

The substrate may be particulate. The particles of the substrate may have a mean particle diameter of less than about 0.5 μm or less than about 100 nm.

In the substrate of formula $Ce_{1-x}M_xO_2$, x may be between about 0.01 and about 0.25, or may be between about 0.1 and about 0.2. For example, in the substrate of formula $Ce_{1-x}M_xO_2$, x may be about 0.01, or may be about 0.05, or may be about 0.1, or may be about 0.15, or may be about 0.2. In some embodiments, x=0. In other embodiments x>0, optionally >0.01 or >0.1. The metallic element, M, may be a lanthanoid, or it may be a transition metal, or it may be an alkaline earth metal, e.g., the metallic element may be a transition metal. The transition metal may be Y. The metallic element may alternatively be a lanthanoid. The lanthanoid may be selected from the group consisting of Sm and Gd. It may be Sm or it may be Gd. The metallic element may be an alkaline earth, e.g., Ca. The metallic element may have a greater affinity for sulfur than for oxygen and/or may enhance the sulfur adsorption ability of the catalyst.

In one embodiment, the substrate is $Ce_{0.9}Sm_{0.1}O_2$. In another embodiment, the substrate is $Ce_{0.9}Gd_{0.1}O_2$. In a further embodiment, the substrate is $Ce_{0.9}Ca_{0.1}O_2$. In yet a further embodiment, the substrate is $Ce_{0.85}Y_{0.15}O_2$. In yet a further embodiment, the substrate is $Ce_{0.85}Sm_{0.15}O_2$.

The catalyst may include regions, commonly discrete or unconnected regions, of a catalytic element disposed on a surface of the substrate. The catalyst may include a catalytic element dispersed on a surface of the substrate, e.g., uniformly or non-uniformly dispersed. The catalyst may include between about 1% and about 40% of a catalytic element by weight, e.g., may include between about 5% and about 20% of a catalytic element by weight. The specific surface area of the substrate may be between about 10 and about 300 $m^2/g$, e.g., between about 50 and about 300 $m^2/g$.

In one embodiment, the present invention provides a catalyst, comprising a catalytic element selected from the group consisting of metallic Co, Fe, Pt, Ru, Rh, Pd, Ni or Ir, disposed on a substrate, wherein said substrate has formula $Ce_{1-x}M_xO_2$, wherein x is between about 0 and about 0.3, optionally between about 0.01 and about 0.3, and wherein M, if present, is a metallic element other than Ce, when used for catalysing a methanation reaction.

In another embodiment, the present invention provides a catalyst, comprising metallic nickel disposed on a substrate, wherein said substrate has formula $Ce_{1-x}M_xO_2$, wherein x is between about 0 and about 0.3, optionally between about 0.01 and about 0.3, and wherein M, if present, is a metallic element other than Ce, when used for catalysing a methanation reaction.

In another embodiment the present invention provides a catalyst including between about 1% and about 40% of a catalytic element selected from the group consisting of metallic Co, Fe, Pt, Ru, Rh, Pd, Ni or Ir by weight of the catalyst disposed on a surface of a substrate, wherein said substrate has formula $CeO_2$, when used for catalysing a methanation reaction; wherein said substrate is particulate and the particles have a mean particle diameter of less than about 0.5 μm.

In another embodiment, the present invention provides a catalyst, comprising a catalytic element selected from the group consisting of metallic Co, Fe, Pt, Ru, Rh, Pd, Ni or Ir disposed on a substrate, wherein said substrate has formula $Ce_{1-x}M_xO_2$, wherein x is between about 0.1 and about 0.3 and wherein M is a metallic element selected from the group consisting of a lanthanoid, a transition metal and an alkaline earth metal, when used for catalysing a methanation reaction.

In another embodiment, the present invention provides a catalyst, comprising discrete regions of a catalytic element disposed on a substrate, wherein said substrate has formula $Ce_{1-x}M_xO_2$, wherein x is between about 0.1 and about 0.3 and wherein M is a metallic element selected from the group consisting of Y, Sm, Gd and Ca, when used for catalysing a methanation reaction.

In another embodiment, the present invention provides a catalyst, comprising a catalytic element disposed on a substrate, wherein said substrate has formula $Ce_{1-x}M_xO_2$, wherein x is between about 0.1 and about 0.3 and wherein M is a metallic element that enhances the sulfur adsorption ability of the catalyst, when used for catalysing a methanation reaction; wherein said substrate has a specific surface area of between about 10 and about 300 $m^2/g$; and wherein said substrate is particulate and the particles have a mean particle diameter of less than about 0.5 μm.

In another embodiment, the present invention provides a catalyst, comprising between about 1% and about 40% by weight of the catalyst of a catalytic element, wherein the catalytic element is metallic nickel, disposed in discrete regions on a surface of a substrate, wherein said substrate has formula $Ce_{1-x}M_xO_2$, wherein x is between about 0.1 and about 0.3 and wherein M is a metallic element selected from the group consisting of a lanthanoid, a transition metal and an alkaline earth metal, when used for catalysing a methanation reaction; wherein said substrate is particulate and the particles have a mean particle diameter of less than about 0.5 μm.

In another embodiment, the present invention provides a catalyst, comprising metallic nickel disposed on a substrate, wherein said substrate has formula $Ce_{0.9}M_{0.1}O_2$, (i.e., x is 0.1), and wherein M is a metallic element selected from the group consisting of Y, Sm, Gd and Ca, when used for catalysing a methanation reaction.

In another embodiment, the present invention provides a catalyst, comprising between about 1% and about 40% by weight of the catalyst of metallic nickel disposed on a surface of a substrate, wherein said substrate has formula $Ce_{0.9}Gd_{0.1}O_2$, (i.e., x is 0.1), when used for catalysing a methanation reaction; wherein said substrate has a specific surface area of between about 10 and about 300 $m^2/g$; and wherein said substrate is particulate and the particles have a mean particle diameter of less than about 0.5 μm.

In another embodiment, the present invention provides a catalyst, comprising metallic nickel disposed on a substrate, wherein said substrate has formula $Ce_{1-x}Ca_xO_2$, wherein x is between about 0.01 and about 0.3, when used for catalysing a methanation reaction.

In another embodiment, the present invention provides a catalyst, comprising metallic nickel disposed on a substrate, wherein said substrate has formula $Ce_{1-x}Gd_xO_2$, wherein x is between about 0.01 and about 0.3, when used for catalysing a methanation reaction.

In another embodiment, the present invention provides a catalyst, comprising between about 1% and about 40% by weight of the catalyst of metallic nickel disposed on a surface of a substrate, wherein said substrate has formula $Ce_{0.9}Ca_{0.1}O_2$, (i.e., x is 0.1), when used for catalysing a methanation reaction; wherein said substrate has a specific surface area of between about 10 and about 300 $m^2/g$; and wherein said substrate is particulate and the particles have a mean particle diameter of less than about 0.5 μm.

In another embodiment, the present invention provides a catalyst, comprising between about 1% and about 40% by weight of the catalyst of metallic nickel disposed on a surface of a substrate, wherein said substrate has formula $Ce_{0.9}Sm_{0.1}O_2$, (i.e., x is 0.1), when used for catalysing a methanation reaction; wherein said substrate has a specific surface area of between about 10 and about 300 $m^2/g$; and wherein said substrate is particulate and the particles have a mean particle diameter of less than about 0.5 μm.

According to a second aspect of the invention there is provided use of a catalyst according to the first aspect above for catalysing a methanation reaction.

In one embodiment, the present invention provides use of a catalyst comprising between about 1% and about 40% of a catalytic element selected from the group consisting of metallic Co, Fe, Pt, Ru, Rh, Pd, Ni or Ir by weight of the catalyst disposed on a surface of a substrate, wherein said substrate has formula $Ce_{1-x}M_xO_2$, wherein x is between about 0.1 and about 0.3 and wherein M is a metallic element selected from the group consisting of a lanthanoid, a transition metal and an alkaline earth metal, for catalysing a methanation reaction.

In another embodiment, the present invention provides use of a catalyst, comprising metallic nickel disposed on a substrate, wherein said substrate has formula $Ce_{0.9}M_{0.1}O_2$, (i.e., x is 0.1), and wherein M is a metallic element selected from the group consisting of Y, Sm, Gd and Ca, for catalysing a methanation reaction.

According to a third aspect of the invention there is provided use of a catalyst according to the first aspect above, said use being for reducing the carbon monoxide content of a gas mixture including carbon monoxide and hydrogen.

According to a fourth aspect of the invention there is provided a method for methanation of a feedstock including carbon monoxide and hydrogen, said method comprising contacting the feedstock with a catalyst according to the first aspect above.

The following options may be used in conjunction with the fourth aspect either individually or in any suitable combination.

The feedstock may additionally include carbon dioxide gas. The feedstock may additionally include steam. The feedstock may include coal gasification effluent and biomass gasification effluent. The feedstock may alternatively include coal gasification effluent or biomass gasification effluent.

The feedstock may additionally include a sulfur-containing gas or vapour. The sulfur-containing gas or vapour may be present at a concentration of about 0.1 to about 5000 ppm. The sulfur-containing gas or vapour may include any one or more of hydrogen sulfide, carbonyl sulfide, sulfur dioxide and an organic thiol.

The molar ratio of hydrogen to carbon monoxide in the feedstock may be between about 4:1 and about 1:1.

Contacting may include passing the feedstock through a packed bed reactor comprising the catalyst, or it may comprise passing the feedstock through a fluidised bed reactor. The pressure of the feedstock during the contacting may be between about 1 bar and about 40 bar. The contacting may be conducted at a temperature of at least about 250° C. The contacting may be conducted at a temperature of between about 250 and about 750° C. The temperature and feedstock flow rate, e.g., gas hourly space velocity, during the contacting may be sufficient to achieve equilibrium conversion of carbon oxides to methane.

The flow rate, e.g., gas hourly space velocity (GHSV) of the feedstock may be between about 1000 h$^{-1}$ and about 100 000 h$^{-1}$.

In one embodiment, the present invention provides a method for methanation of a feedstock including carbon monoxide and hydrogen, said method comprising contacting the feedstock with a catalyst according to the first aspect above, wherein the feedstock additionally includes a sulfur-containing gas or vapour present at a concentration of about 0.1 to about 5000 ppm and wherein the contacting is conducted at a temperature of at least about 250° C.

In another embodiment, the present invention provides a method for methanation of a feedstock including carbon monoxide, hydrogen and carbon dioxide, said method comprising contacting the feedstock with a catalyst according to the first aspect above, wherein the feedstock additionally includes a sulfur-containing gas or vapour present at a concentration of about 0.1 to about 5000 ppm and wherein the contacting is conducted at a temperature of between about 250 and about 750° C.

In another embodiment, the present invention provides a method for methanation of a feedstock including carbon monoxide and hydrogen, wherein the molar ratio of hydrogen to carbon monoxide in the feedstock is between about 4:1 and about 1:1, said method comprising contacting the feedstock with a catalyst according to the first aspect above, wherein the feedstock additionally includes a sulfur-containing gas or vapour present at a concentration of about 0.1 to about 5000 ppm and wherein the contacting is conducted at a temperature of between about 250 and about 750° C. wherein the pressure of the feedstock during contacting is between about 1 bar and about 40 bar.

In another embodiment, the present invention provides a method for methanation of a feedstock including carbon monoxide and hydrogen, said method comprising contacting the feedstock with a catalyst comprising metallic nickel disposed on a substrate, wherein said substrate has formula $Ce_{1-x}M_x(O_2)$, wherein x is between about 0.1 and about 0.3 and wherein M is a metallic element selected from the group consisting of a lanthanoid, a transition metal and an alkaline earth metal, wherein the feedstock includes coal gasification effluent or biomass gasification effluent and further includes a sulfur-containing gas or vapour at a concentration of about 0.1 to about 5000 ppm.

In another embodiment, the present invention provides a method for methanation of a feedstock including carbon monoxide and hydrogen, said method comprising contacting the feedstock with a catalyst comprising metallic nickel disposed on a substrate, wherein said substrate has formula $Ce_{0.9}M_{0.1}O_2$, (i.e., x is 0.1), and wherein M is a metallic element selected from the group consisting of Sm, Gd and Ca, wherein said substrate has a specific surface area of between about 10 and about 300 m$^2$/g; and wherein said substrate is particulate and the particles have a mean particle diameter of less than about 0.5 μm, wherein the feedstock includes coal gasification effluent or biomass gasification effluent and further includes a sulfur-containing gas or vapour at a concentration of about 0.1 to about 5000 ppm.

According to a fifth aspect of the invention there is provided a method for reducing the carbon monoxide content of a gas mixture including carbon monoxide and hydrogen, said method comprising contacting the feedstock with a catalyst according to the first aspect above.

According to a sixth aspect of the invention there is provided use of a substrate of formula $Ce_{1-x}M_xO_2$, wherein x is between about 0 and about 0.3, optionally between about 0.01 and about 0.3, and wherein M, if present, is a metallic element other than Ce, for reducing poisoning of a catalytic element by a sulfur-containing gas or vapour.

According to a seventh aspect of the invention there is provided a method for reducing poisoning of a catalytic element by a sulfur-containing gas or vapour, said method comprising depositing said catalytic element on a substrate, wherein said substrate has formula $Ce_{1-x}M_xO_2$, wherein x is between about 0 and about 0.3, optionally between about 0.01 and about 0.3, and wherein M, if present, is a metallic element other than Ce.

The following options may be used in conjunction with the seventh aspect either individually or in any suitable combination.

Said depositing may be conducted before exposing said catalytic element to the sulfur-containing gas or vapour. Said depositing may be such that the catalytic element is present in discrete regions on the substrate.

BRIEF DESCRIPTION OF DRAWINGS

Preferred embodiments of the present invention will now be described, by way of example only, with reference to the accompanying figures wherein.

DEFINITIONS

Figure 1:
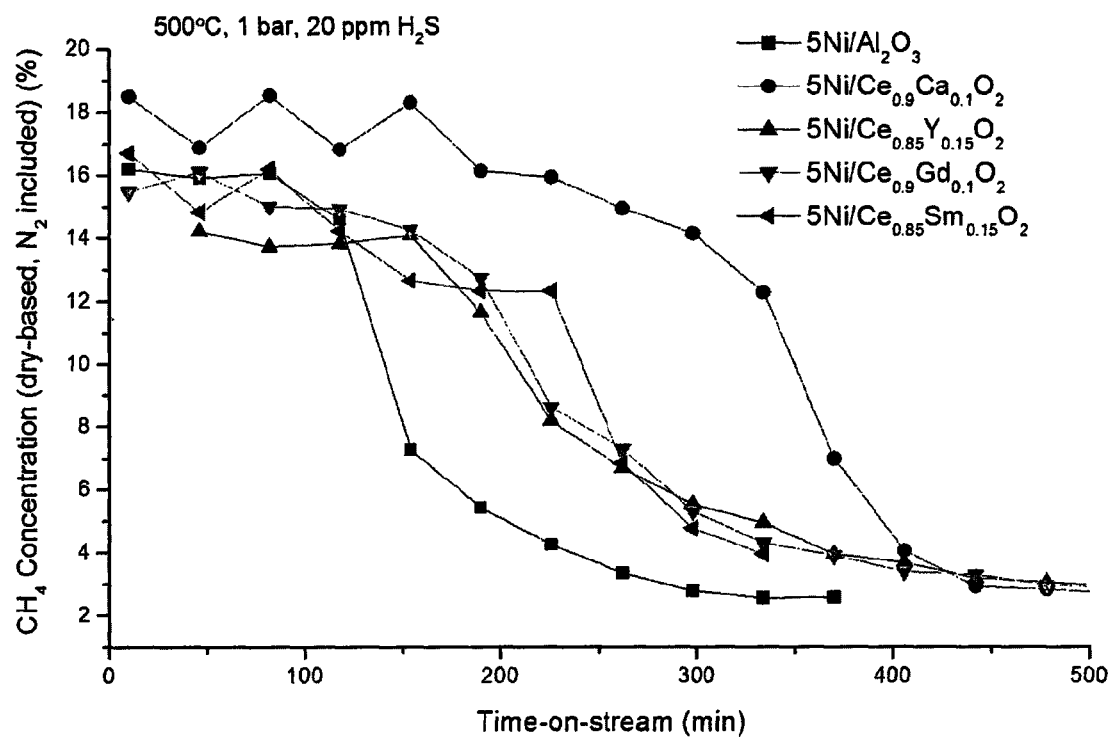
FIG. 1 shows the results for long-term stability test of catalysts according to the present invention (Ni/$Ce_{0.9}Gd_{0.1}O_2$; Ni/$Ce_{0.9}Ca_{0.1}O_2$; Ni/$Ce_{0.85}Y_{0.15}O_2$; Ni/$Ce_{0.85}Sm_{0.15}O_2$) compared to a catalyst known in the art (Ni/$Al_2O_3$). Alterations of the methane concentrations are plotted as a function of time-on-stream. Feed composition: 10% $H_2O$, 10% $N_2$, 40% $H_2$, 20% CO, 16% $CO_2$, 4% $CH_4$, 20 ppm $H_2S$; T=500° C.; SV=20,000 h$^{-1}$.

As used in this application, the singular form "a", "an" and "the" include plural references unless the context clearly dictates otherwise. For example, the phrase "a catalyst" also includes a plurality of catalysts.

As used herein, the term "comprising" means "including." Variations of the word "comprising", such as "comprise" and "comprises," have correspondingly varied meanings. As used herein, the terms "including" and "comprising" are non-exclusive. Thus, for example, a feedstock "including" carbon monoxide and hydrogen may consist exclusively of carbon monoxide and hydrogen or it may contain one or more additional components (e.g. carbon dioxide). Similarly, a method "comprising" contacting a feedstock with a catalyst may consist exclusively of contacting the feedstock with the catalyst, or it may contain one or more additional steps (e.g., a feedstock analysis step). As used herein, the terms "including" and "comprising" do not imply that the specified integer(s) represent a major part of the whole.

As used herein the term "plurality" means more than one. In certain specific aspects or embodiments, a plurality may mean 2, 3, 4, 5, 6, 7, 8, 9, 10, 15, 20, 30, 40, 50, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more, and any integer derivable therein, and any range derivable therein.

As used herein, the terms "methanation" and "methanation reaction" refer to a reaction that generates methane, and in particular, these terms refer to the reaction between hydrogen and one or more oxides of carbon to form methane. Accordingly, the terms "methanation" and "methanation reaction" may refer to the reaction between carbon monoxide and hydrogen to form methane and water, or the reaction between carbon dioxide and hydrogen to form methane and water, or a combination of both of these reactions.

As used herein, the term "catalytic element" may refer to any element which is recognised as having catalytic capabilities, e.g., an element that can catalyse a methanation reaction. As used herein, the term "metallic nickel", or "metallic cobalt", or "metallic palladium" etc. refers to the metal, e.g., nickel, cobalt, or palladium, etc. in its elemental state (i.e., Ni(0), Co(0), Pd(0), etc.).

As used herein, the nomenclature x % Metal/$Ce_{1-x}M_xO_2$, e.g., 5% Ni/$Ce_{0.9}Ca_{0.1}$, is taken to mean x % by weight of the Metal, e.g., Ni, disposed or dispersed on a surface of a substrate of formula $Ce_{1-x}M_xO_2$.

It will be understood that use the term "about" herein in reference to a recited numerical value includes the recited numerical value and numerical values within plus or minus ten percent of the recited value. The term "about 0" may refer a range of between exactly 0 and about 0.01.

It will be understood that use of the term "between" herein when referring to a range of numerical values encompasses the numerical values at each endpoint of the range. For example, a temperature of between 250 and 750° C. is inclusive of a temperature of 250° C. and a temperature of 750° C.

For the purposes of description all documents referred to herein are hereby incorporated by reference in their entirety unless otherwise stated.

DETAILED DESCRIPTION

The present invention provides catalytic element-based methanation catalysts including, e.g., metallic Ni or metallic Co, Fe, Pt, Ru, Rh, Pd, or Ir, disposed on a substrate when used for catalysing a methanation reaction. The substrate has formula $Ce_{1-x}M_xO_2$, wherein x is between about 0 and about 0.3, optionally between about 0.01 and about 0.3, and M, if present, is a metallic element other than Ce. The inventors have discovered that these catalysts have enhanced sulfur resistance when used to catalyse methanation reactions, and are thus advantageously adapted for use with, for example, sulfur-containing feedstocks.

The following detailed description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

Methanation

The methanation reaction as referred to herein involves the generation of methane from a feedstock including an oxide of carbon and hydrogen, e.g., carbon monoxide and hydrogen. The associated exothermic chemical transformation may be represented by Equation 1:

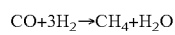   Equation 1

The methanation reaction in Equation 1 is the reverse reaction of steam reforming of methane.

Additionally, in the presence of carbon dioxide, the methanation reaction may also generate methane via Equation 2:

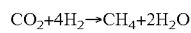   Equation 2

Catalyst

The substrate of the catalyst according to the present invention may be particulate. The particles of the substrate may have a known mean particle diameter as measured using techniques such as microscopy, light scattering or any other suitable method for measuring particle diameter known to those skilled in the art. The shape of the substrate particles may be spherical, acicular, flat, flaky, prismoidal, polyhedral, fibrous, irregular, spheroidal, or granular. As used herein, the term "mean particle diameter" may refer to the average diameter of a plurality of particles, e.g., the average hydrodynamic diameter of a plurality of particles, or may be taken to be the collective average of the minimum and maximum diameters of a plurality of particles, or the term "mean particle diameter" may refer to the average of the minimum and maximum diameter of a single particle. For example, the particles of the substrate may have a mean particle diameter of less than about 0.5 µm, or less than about 0.4 µm about 0.3 µm, about 0.2 µm, about 0.1 µm (i.e., about 100 nm), about 90 nm, about 80 nm, about 70 nm, about 60 nm or less than about 50 nm. The particles of the substrate may have a mean particle diameter of between about 0.5 µm and about 0.1 µm, or between about 0.25 µm and 75 nm, or between about 100 nm and about 10 nm. The particles of the substrate may have a mean particle diameter of about 0.4 µm, about 0.3 µm, about 0.2 µm, about 0.1 µm (i.e., about 100 nm), about 90 nm, about 80 nm, about 70 nm, about 60 nm or about 50 nm.

In the substrate of formula $Ce_{1-x}M_xO_1$, x may be between about 0 and about 0.3. For example, x may be between about 0 and about 0.1, or may be between about 0.01 and about 0.1, or may be between about 0.05 and about 0.25, or may be between about 0.1 and about 0.3, or may be between about 0.1 and about 0.2, or may be between about 0.01 and about 0.25. For example, x may be 0, or may be about 0.01, about 0.05, about 0.1, about 0.15, about 0.2, about 0.25, or about 0.3. Where x is 0, the substrate is of formula $CeO_2$. Where x is 0.1, the substrate is of formula $Ce_{0.9}M_{0.1}O_2$ wherein M is a metallic element other than Ce. Substrates of formula $Ce_{1-x}M_xO_2$, wherein x may be between about 0.01 and about 0.3 and M, if present, is a metallic element other than Ce, may be synthesised using any suitable method known in the art. Materials of formula $Ce_{1-x}M_xO_2$ may include Ce(IV) ions and M ions in any suitable oxidation state, e.g., Gd(III), Ca(II), etc. It will be understood by those in the art that materials available for purchase or materials otherwise referred to as having the formula $Ce_{1-x}M_xO_2$ may also be referred to or sold as $CeO_2$-$M_2O_3$ (where M=any $M^{3+}$ ion, e.g., Gd, Sm) or $CeO_2$-MO (where M=any $M^{2+}$ ion, e.g., Ca) or M:$CeO_2$ to denote doping of ceria with one or more metallic elements, M. It will also be understood that materials of formula $Ce_{1-x}M_xO_2$ may comprise vacancies, e.g., oxygen vacancies, to maintain charge balance. For convenience, such materials are described herein as having the formula $Ce_{1-x}M_xO_2$, although for materials where M has an oxidation state of less than (+IV), the ratio (Ce+M):O may actually vary from 1:2, e.g., the ratio (Ce+M):O may be about 1:1.95, or about 1:1.9, or about 1:1.85, etc. In some embodiments, the substrate of formula $Ce_{1-x}M_xO_2$ may be represented as, e.g., $Ce_{1-x}M_xO_{2-y}$, where $0 \leq y < 0.5$, to represent the oxygen vacancies present and hence the charge-balanced stoichiometry of these materials. The value of 'y' may be about 0 to about 0.5, or about 0 to about 0.1, about 0 to about 0.2, about 0.1 to about 0.3, about 0 to 0.05, about 0.001 to about 0.05, about 0.001 to about 0.01, about 0.001 to about 0.5 or about 0.3 to about 0.5. It may for example be about 0, 0.001, 0.002, 0.005, 0.01, 0.02, 0.05, 0.1, 0.15, 0.2, 0.25, 0.3, 0.35, 0.4, 0.45 or 0.5.

In the substrate of formula $Ce_{1-x}M_xO_2$, M, if present, may be a metallic element. Any suitable metal may be chosen, for example, the metallic element may be a lanthanoid, a transition metal, or an alkaline earth metal. The metallic element may therefore be a transition metal, e.g., may be Y. The metallic element may be a lanthanoid, e.g., may be Sm or may be Gd or may be a mixture of Sm and Gd. The metallic element may be an alkaline earth metal, e.g., may be Ca. The metallic element may be a mixture of two or more metallic elements, wherein, for example, the formula $Ce_{1-x}M_xO_2$ may be represented by formula $Ce_{1-x-n}M^1_xM^2_nO_2$, wherein the sum of x and n may be between about 0.01 and about 0.3 and $M^1$ and $M^2$ are each, independently, selected from the group consisting of a lanthanoid, a transition metal and an alkaline earth metal. Advantageously, the one or more metallic elements enhance the sulfur adsorption ability of the catalyst and/or increase the oxygen mobility in the $Ce_{1-x}M_xO_2$ material. Further, the one or more metallic elements may have a greater affinity for sulfur than for oxygen.

The catalyst as described herein may comprise regions of a catalytic element disposed on a surface of the substrate. For example, the catalyst as described herein may comprise regions of metallic Ni or metallic Co, Fe, Pt, Ru, Rh, Pd, or Ir disposed on a surface of the substrate. Mixtures of catalytic metals, at least one of which is catalytic, may also be used. The catalyst may additionally or alternatively comprise a catalytic element dispersed on a surface of the substrate. For example, the catalyst as described herein may comprise regions of metallic Ni or metallic Co, Fe, Pt, Ru, Rh, Pd, or Ir dispersed on a surface of the substrate. The term 'region' as used herein may refer to discrete areas of a catalytic element disposed or dispersed on a surface of the substrate, e.g., non-connected, non-contiguous areas of metallic Ni or metallic Co, Fe, Pt, Ru, Rh, Pd, or Ir, or it may refer to continuous areas of a catalytic element disposed or dispersed on a surface of the substrate, e.g., interconnected or contiguous areas of metallic Ni or metallic Co, Fe, Pt, Ru, Rh, Pd, or Ir, as viewed using any suitable technique known in the art, for example, microscopy.

The catalytic element disposed on or dispersed on a surface of the substrate may be particulate. Accordingly, a region of catalytic element may include, e.g., one metallic nickel or metallic Co, Fe, Pt, Ru, Rh, Pd, or Ir particle or may include, e.g., a plurality of metallic nickel or metallic Co, Fe, Pt, Ru, Rh, Pd, or Ir particles. Where the regions of catalytic element include a plurality of metallic nickel or metallic Co, Fe, Pt, Ru, Rh, Pd, or Ir particles, the metallic nickel or metallic Co, Fe, Pt, Ru, Rh, Pd, or Ir particles may be uniformly or substantially uniformly disposed or dispersed throughout the region(s) on the surface of the substrate, or may be non-uniformly disposed or dispersed throughout the region(s) on the surface of the substrate, wherein the regions are as described in the preceding paragraph. The term 'region' may thus encompass one or more metallic nickel or metallic Co, Fe, Pt, Ru, Rh, Pd, or Ir particles disposed on a surface of the substrate, or two or more metallic nickel or metallic Co, Fe, Pt, Ru, Rh, Pd, or Ir particles dispersed on a surface of the substrate.

The shape of the catalytic element particles may be spherical, acicular, flat, flaky, prismoidal, polyhedral, fibrous, irregular, spheroidal, or granular. The catalytic element particles may have a mean particle diameter of about 2 to about 100 nm, or about 2 to about 10, about 10 to about 40, about 20 to about 50, about 30 to about 60, about 50 to about 80, or about 70 to about 100 nm, e.g., about 2, about 5, about 10, about 20, about 40, about 60, about 80, or about 100 nm. In the event that the catalytic element particles are not spherical, the diameter of a particle may be taken as the hydrodynamic diameter, or may be taken to be the minimum diameter of a particle (e.g., a thickness), the maximum diameter of a particle (e.g., a length) or the mean diameter of a particle. The particle diameter of the catalytic element particles may be determined using well-established techniques including transmission electron microscopy and X-ray powder diffraction. The catalytic element may be disposed on or dispersed on the substrate using any suitable synthetic methods, for example, by conventional wet impregnation methods using salts of nickel, e.g., Ni(NO$_3$)$_2$.xH$_2$O, or other suitable salts of Co, Fe, Pt, Ru, Rh, Pd, or Ir and subsequent reduction to metallic nickel or metallic Co, Fe, Pt, Ru, Rh, Pd, or Ir in situ, for example, under a hydrogen atmosphere at elevated temperatures.

In alternative embodiments, the substrate may be monolithic rather than particulate. In such embodiments, the regions of catalytic element, e.g., metallic Ni or metallic Co, Fe, Pt, Ru, Rh, Pd, or Ir disposed on a surface of the substrate may be in the form of one or more layers (optionally discontinuous layers) of catalytic element or one or more veins of catalytic element on a surface of the monolithic substrate. The layer or vein of catalytic element may include particles of catalytic element as described above.

The catalyst may comprise between about 1% and about 40% catalytic element, e.g., metallic Ni or metallic Co, Fe, Pt, Ru, Rh, Pd, or Ir by weight. For example, the catalyst may comprise between about 1% and about 10% metallic nickel by weight, or between about 5% and 20% by weight, or between about 10% and 30% by weight, or between about 30% and 40% metallic nickel by weight, e.g., the catalyst may comprise about 1% metallic nickel by weight, or about 5%, about 8%, about 10%, about 12%, about 14%, about 16%, about 18%, about 20%, about 25%, about 30%, about 35% or about 40% metallic nickel by weight. In alternative embodiments, the catalyst may comprise between about 1% and about 40% metallic Co, Fe, Pt, Ru, Rh, Pd, or Ir by weight, e.g., between about 1% and about 10%, or between about 5% and 20%, or between about 10% and 30%, or between about 30% and 40% by weight metallic Co, Fe, Pt, Ru, Rh, Pd, or Ir. Suitable methods for determining metal content in materials are known in the art.

The catalyst may have a metallic surface area, as measured in $m^2$ catalytic element per gram of catalyst, of between about 0.1 and about 3.0 $m^2/g$, or between about 0.1 and about 1.5 $m^2/g$, or between about 1 and about 2 $m^2/g$, or between about 2 and about 3 $m^2/g$. For example, the metallic surface area in $m^2$ per gram of catalyst may be about 0.1 $m^2/g$, about 0.5 $m^2/g$, about 1.0 $m^2/g$, about 1.5 $m^2/g$, about 2.0 $m^2/g$, about 2.5 $m^2/g$, or about 3.0 $m^2/g$. The catalyst may have a metallic surface area, as measured in $m^2$ metallic catalytic element per gram of metal, of between about 5 and about 50 $m^2/g$, or between about 5 and about 20 $m^2/g$, or between about 20 and about 35 $m^2/g$, or between about 30 and about 50 $m^2/g$. For example, the metallic surface area in $m^2$ per gram of metal may be about 5 $m^2/g$, about 10 $m^2/g$, about 15 $m^2/g$, about 20 $m^2/g$, about 25 $m^2/g$, about 30 $m^2/g$, about 35 $m^2/g$, about 40 $m^2/g$, about 45 $m^2/g$, or about 50 $m^2/g$.

The specific surface area of the substrate may be between about 10 and about 300 $m^2/g$ as measured, for example, using BET methods well known in the art. For example, the specific surface area of the substrate may be between about 10 $m^2/g$ and about 100 $m^2/g$, or between about 50 $m^2/g$ and about 300 $m^2/g$, or between about 100 $m^2/g$ and about 200 $m^2/g$, or between about 200 $m^2/g$ and about 300 $m^2/g$, or between about 150 and 250 $m^2/g$, e.g., the specific surface area of the substrate may be about 10 $m^2/g$, about 50 $m^2/g$, about 75 $m^2/g$, about 100 $m^2/g$, about 125 $m^2/g$, about 150 $m^2/g$, about 175 $m^2/g$, about 200 $m^2/g$, about 225 $m^2/g$, about 250 $m^2/g$, about 275 $m^2/g$ or about 300 $m^2/g$.

Use

The catalyst according to the invention and as described above in the section entitled 'Catalyst' may be used for catalysing a methanation reaction.

The catalyst according to the invention and as described above in the section entitled 'Catalyst' may be used for reducing the carbon monoxide content of a gas mixture including carbon monoxide and hydrogen.

The substrate of formula $Ce_{1-x}M_xO_2$, wherein x is between about 0 and about 0.3, optionally between about 0.01 and about 0.3, and wherein M, if present, is a metallic element other than Ce as described above in the section entitled 'Catalyst' may be used for reducing poisoning of a catalytic element by a sulfur-containing gas or vapour.

Method

According to the present invention, a method is provided for methanation of a feedstock including carbon monoxide and hydrogen, said method comprising contacting the feedstock with a catalyst as described above in the section entitled 'Catalyst'. A method is also provided for reducing the carbon monoxide content of a gas mixture including carbon monoxide and hydrogen, said method comprising contacting the feedstock with a catalyst as described above in the section entitled 'Catalyst'.

The feedstock for input into the method of the invention may include molecular hydrogen and carbon monoxide. The feedstock may additionally include any other gas or vapour, for example, carbon dioxide gas, steam (i.e., water vapour), molecular nitrogen, methane, or a mixture of any two or more of these gases or vapours. The molar ratio of molecular hydrogen to carbon monoxide in the feedstock may be between about 4:1 and about 1:1, between about 4:1 and about 3:1, between about 4:1 and about 2:1, between about 3:1 and about 2:1, or between about 3:1 and about 1:1, e.g., the molar ratio of molecular hydrogen to carbon monoxide in the feedstock may be about 4:1, about 3.5:1, about 3:1, about 2.5:1, about 2:1, about 1.5:1 or about 1:1. The ratio may depend on the source of the feedstock. The concentration of carbon monoxide in the gas mixture may be about 10% to about 40%, or about 10 to 30%, 20 to 40% or 20 to 30%, e.g., about 10%, 15%, 20%, 25%, 30%, 35% or 40%. This percentage may be by volume.

The feedstock for input into the method of the invention may include, or may consist essentially of, coal gasification effluent, biomass gasification effluent, or a mixture of both of these. Coal gasification effluent may be the product of the gasification of black and/or brown coal or petroleum coke in the presence of oxygen, steam (water vapour) and heat and may optionally include any by-products of the coal gasification process. Biomass gasification effluent may be the product of the gasification of any suitable biomass, e.g., woody plant matter or components thereof in the form of pellets or chips, fibrous plant matter or components thereof, including fruits, flowers, grains, grasses, herbaceous crops, wheat straw, switchgrass, salix, sugarcane bagasse, cotton seed hairs, leaves, bark, needles, logs, roots, saplings, short rotation woody crops, shrubs, switch grasses, trees and vines, and grains or grain processing wastes (e.g., wheat/oat hulls, corn fines etc.), waste or byproduct streams from wood products, sawmill and paper mill discards and off-cuts, sawdust, and particle board or from wood-related materials and woody wastes and industrial products, e.g., pulp, paper (e.g., newspaper) papermaking sludge, cardboard, textiles and cloths, dextran, and rayon, agricultural crops or agricultural crop residues, sewage sludge, municipal waste, and/or plastics, in the presence of oxygen, steam (water vapour) and heat and may optionally include any by-products of the biomass gasification process.

The feedstock as described in the preceding paragraphs may additionally include a sulfur-containing gas or vapour. The sulfur containing gas may be present at a total concentration of at least about 0.1 ppm, or at least about 0.2, 0.3, 0.4, 0.5, 1, 2, 3, 4, 5, 10, 15, 20, 25, 30, 35, 40, 45, 50, 60, 70, 80, 90, 100, 200, 300, 400, 500, 1000, 1500, 2000, 2500, 3000, 3500, 4000, 4500, or 5000 ppm, or at between about 0.1 to about 5000 ppm, or between about 1 to about 50 ppm, or between about 20 to about 80 ppm, or between about 50 to about 100 ppm, or between about 100 to about 500, or between about 500 to about 1000 ppm, or between about 1000 to about 2000 ppm, or about 2000 to about 3000 ppm, or about 3000 to about 4000 ppm, or about 4000 to about 5000 ppm, or at a total concentration of about 0.1, 0.2, 0.3, 0.4, 0.5, 1, 2, 3, 4, 5, 10, 15, 20, 25, 30, 35, 40, 45, 50, 60, 70, 80, 90, 100, 200, 300, 400, 500, 1000, 1500, 2000, 2500, 3000, 3500, 4000, 4500, or 5000 ppm. The sulfur-containing gas may be hydrogen sulfide, or may be carbonyl sulfide, or may be organic thiols (e.g. methane thiol, ethane thiol, thiophenol etc.), or may be an oxide of sulfur, e.g., sulfur dioxide, or may be a mixture of any two or more of these. In the present invention, ppm of a sulfur-containing gas is by volume, i.e., is taken to mean microlitres of gas per litre of air (µL/L).

It will be understood that the feedstock as described in the preceding paragraphs may be analysed prior to contacting the feedstock with a catalyst according to the invention to determine the composition of the feedstock, and in particular, the concentrations of gases present, e.g., concentration of hydrogen gas, carbon monoxide, carbon dioxide, sulfur-containing gases, steam (i.e., water vapour), molecular nitrogen, methane, etc. The concentration of any one or more of these gases may be altered, e.g., by removal of some or all of any one or more of the gases, or by supplementing the concentration of any one or more of the gases with additional gas(es) obtained or derived from any suitable source. For example, if the ratio of hydrogen to carbon monoxide in the feedstock derived from biomass or coal gasification effluent is about 2:1, and it is desired to use a ratio of hydrogen to carbon monoxide of 3:1 in the method according to the invention, additional hydrogen gas may be added to the feedstock prior to contacting the feedstock with the catalyst.

In the method according to the invention, contacting may comprise passing the feedstock through a packed bed reactor including the catalyst, or over or past a catalyst disposed in a reactor. The reactor may include one or more (e.g., 1, 2, 3, 4 or 5) packed reactor beds arranged in series or in parallel. The packed bed reactor or reactors may operate under isothermal or adiabatic conditions. The catalyst may be packed in beds, rods, or plates, or may be coated on the inside surface of a reactor vessel or on some other surface thereof. The catalyst may be coated on any one or more of honeycomb catalyst structures, porous metal catalyst structures, or ceramic matrix catalyst structures. The contacting method may instead include bubbling the feedstock through a slurry including the catalyst, or include passing the feedstock through a fluidised bed reactor including the catalyst.

During contacting, the feedstock may be at a pressure of between about 1 to about 40 bar, or between about 1 and about 5 bar, between about 5 and about 10 bar, between about 5 and about 20 bar, between about 10 and about 25 bar, between about 20 and about 35 bar, or between about 25 and about 40 bar, e.g., the feedstock may be at a pressure of about 1, 2, 3, 3.5, 4, 5, 6, 7, 8, 9, 10, 15, 20, 25, 30, 35 or 40 bar. The flow rate, e.g., gas hourly space velocity, of the feedstock may be between about 1000 $h^{-1}$ and about 100 000 $h^{-1}$, or between about 1000 $h^{-1}$ and about 10 000 $h^{-1}$ or between about 10 000 $h^{-1}$ and about 50 000 $h^{-1}$, or between about 50 000 $h^{-1}$ and about 100 000 $h^{-1}$, e.g., it may be about 1000, 5000, 10 000, 20 000, 30 000, 40 000, 50 000, 60 000, 70 000, 80 000, 90 000, or 100 000 $h^{-1}$. At times, other flow rates may be used. These flow rates may be a space velocity (SV; volumetric flow rate/catalyst volume) or a gas hourly space velocity (GHSV; reactant gas flow rate/catalyst volume). The contacting may be conducted at a temperature of at least about 250° C., or at least about 300, 350, 400, 450, 500, 550 or 600° C., or between about 250 and about 750° C., or between about 250 and about 400° C., or between about 350 and about 600° C., or between about 500 and about 750° C., e.g., it may be about 400, about 450, about 500, about 550, about 600, about 650, about 700, or about 750° C. The temperature and feedstock flow rate during the contacting method may be chosen to be sufficient to achieve equilibrium conversion of carbon oxides to methane, or at least 50%, at least 60%, at least 70%, at least 80%, or at least 90% of the equilibrium conversion of carbon oxides to methane.

As disclosed herein there is provided a method for reducing the carbon monoxide content of a gas mixture including carbon monoxide and hydrogen, said method comprising contacting the feedstock with a catalyst as described above in the section entitled 'Catalyst'. The gas mixture may include any gases in addition to carbon monoxide and molecular hydrogen, e.g., carbon dioxide gas, steam (i.e., water vapour), molecular nitrogen, methane, or a mixture of any two or more of these. Reducing the carbon monoxide content of such a gas mixture may be desired where carbon monoxide would act as a poison in industrial processes or where it would be toxic or poisonous to animals. It is envisaged that the methods described herein for catalysing a methanation reaction would be applicable to the method of reducing the carbon monoxide content of a gas mixture.

According to the present invention, a method is provided for reducing poisoning of a catalytic element by a sulfur-containing gas or vapour, said method comprising depositing a catalytic element as described above in the section entitled 'Catalyst' on a substrate, wherein said substrate has formula $Ce_{1-x}M_xO_2$, wherein x is between about 0 and about 0.3, optionally between about 0.01 and about 0.3, and wherein M, if present, is a metallic element other than Ce. The substrate of formula $Ce_{1-x}M_xO_2$, may be as described above in the section entitled 'Catalyst'.

In the method for reducing poisoning of a catalytic element by a sulfur-containing gas or vapour, said depositing may be conducted before exposing said catalytic element to the sulfur-containing gas or vapour. Further, said depositing may be such that the catalytic element is present in discrete regions on the substrate, for example, discrete regions as described herein for catalytic elements in the section entitled 'Catalyst'. 'Depositing' may be effected using any suitable technique known in the art, for example, conventional wet impregnation methods using salts of the catalytic element. It may comprise subsequent in situ reduction of the salt of the catalytic element to a metallic form of the catalytic element, for example, under a hydrogen atmosphere at elevated temperatures. Exposing said catalytic element to the sulfur-containing gas or vapour may comprise contacting a feedstock comprising the sulfur-containing gas or vapour with the catalytic element and/or substrate as described in this section entitled 'Methods'.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be described with reference to specific examples, which should not be construed as in any way limiting.

Synthesis

The $Ni/Ce_{1-x}M_xO_2$ catalysts, wherein x is between about 0 and about 0.3, optionally between about 0.01 and about 0.3, and wherein M, if present, is a metallic element other than Ce, were prepared by conventional wet impregnation methods using $Ni(NO_3)_3 \cdot 6H_2O$ as the Ni precursor and commercially available $Ce_{1-x}M_xO_2$ (Sigma Aldrich).

Catalytic Results

Cerium oxide is well known for its oxygen storage and redox properties. The partial replacement of Ce with some other components, for example, Zr, Gd, Sm etc is believed to increase the stability, oxygen storage ability and reducibility. In this example, various nano-size cerium oxides with dopants of Y, Sm, Gd and Ca, nano- and micro-size $CeO_2$ were used as catalyst supports. FIG. 1 shows the results of the performance of 5% Ni supported on $Al_2O_3$, $Ce_{0.9}Ca_{0.1}O_2$, $Ce_{0.9}Gd_{0.1}O_2$, $Ce_{0.85}Y_{0.15}O_2$ and $Ce_{0.85}Sm_{0.15}O_2$ in the gas stream containing 20 ppm of $H_2S$ at 500° C. and 1 bar. The concentration of $CH_4$ over 5% $Ni/Al_2O_3$ decreases from the 22% (dry based) at the beginning of the reaction to the initial 4.4% which indicates the complete deactivation of catalyst at around 150 min. It takes about 350 minutes to deactivate 5% Ni/Ce$_{0.9}$Gd$_{0.1}$O$_2$. However, some activity still remains over the 5% Ni/Ce$_{0.9}$Ca$_{0.1}$O$_2$ catalyst at 470 minutes.

The spent catalysts were analysed by XPS, TPH, S analyser and TOF-SIMS. Taking into account the Ni dispersion measured by H$_2$ adsorption (Table 1), the ratios of the exposed number of Ni atoms to the total number of sulfur atoms on the spent catalysts are calculated and listed in Table 2. Ni dispersion refers to the ratio of the exposed number of Ni atoms to the total number of Ni atoms in the catalyst.

TABLE 1

Ni dispersion (Micromeritics ASAP 2020 Surface Area and Porosity Analyser)

| Samples | Nominal metal loading | Ni dispersion | Ni surface area (m$^2$/g cat) | Ni surface area (m$^2$/g Ni) |
|---|---|---|---|---|
| 5% Ni/Al$_2$O$_3$ | 5% | 1.5% | 0.51 | 10.2 |
| 5% Ni/Ce$_{0.9}$Gd$_{0.1}$O$_2$ | 5% | 5.9% | 1.96 | 39.2 |

TABLE 2

The ratio of surface Ni to total sulfur on the spent catalysts

| Reaction conditions | Sample name | S on spent catalysts | Ni dispersion | Ni:S |
|---|---|---|---|---|
| 20 ppm, 500° C. 180 min | 5% Ni/Al$_2$O$_3$ | 352.2 ppm | 1.5% | 1:0.83 |
| 20 ppm, 500° C. 900 min | 5% Ni/Ce$_{0.9}$Gd$_{0.1}$O$_2$ | 1900 ppm | 5.90% | 1:1.25 |

According to the following reaction (Equation (3)), one Ni is supposed to adsorb one S. Without being bound by theory, it is thought that owing to the size of the sulfide ion, the sulfur capacity is less than one sulfur atom per nickel atom. The Ni:S ratio is 1:0.83 on the 5% Ni/Al$_2$O$_3$.

$$H_2S\ (gas) + Ni \rightarrow Ni\text{---}S + H_2\ (gas) \quad \text{Equation 3}$$

Figure 2:
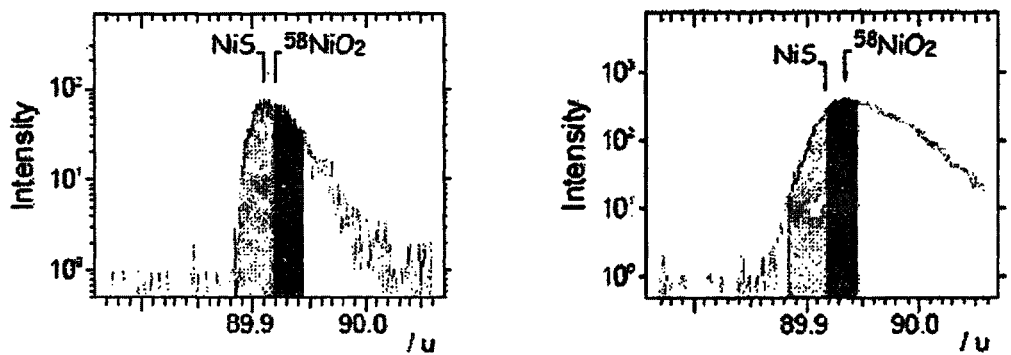
FIG. 2 shows the positive SIMS spectrum of spent 5% Ni/$Al_2O_3$ (left) and 5% Ni/$Ce_{0.9}Gd_{0.1}O_2$ (right).
Figure 3:
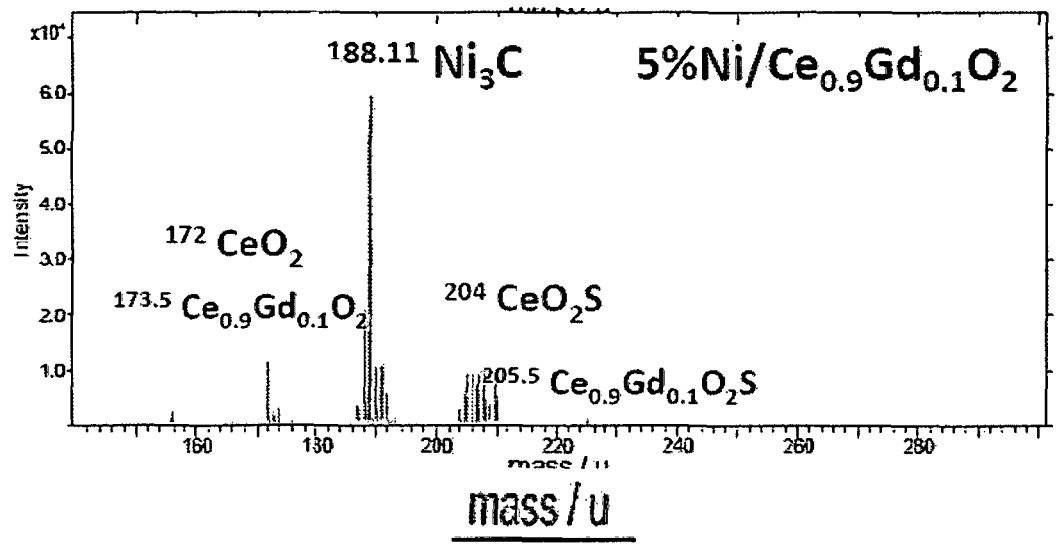
FIG. 3 shows the positive SIMS spectrum of spent 5% Ni/$Ce_{0.9}Gd_{0.1}O_2$.

An unusual Ni:S ratio of 1:1.25 is observed on 5% Ni/Ce$_{0.9}$Gd$_{0.1}$O$_2$ indicating that other adsorption sites for H$_2$S must exist besides Ni. It is thought that ceria can be an adsorbent of H$_2$S to form Ce$_2$O$_2$S. The results obtained from TOF-SIMS may shed some light. The SIMS spectrum in FIG. 2 show that NiS is more easily detected on 5% Ni/Al$_2$O$_3$ than on 5% Ni/Ce$_{0.9}$Gd$_{0.1}$O$_2$ despite the fact that there are many more surface active Ni sites (metal dispersion 5.9% vs 1.5%) and sulfur content (0.19% vs 352 ppm) on 5% Ni/Ce$_{0.9}$Gd$_{0.1}$O$_2$ than on 5% Ni/Al$_2$O$_3$. Therefore, it is reasonable to propose that sulfur is more strongly bonded to Ni on Al$_2$O$_3$ than on Ce$_{0.9}$Gd$_{0.1}$O$_2$. Ceria is thought to react with H$_2$S and form Ce$_2$O$_2$S according to Equation 4. Indeed, peaks attributed to Ce$_2$O$_2$S and respective fragments can be observed from the SIMS spectrum of spent 5% Ni/Ce$_{0.9}$Gd$_{0.1}$O$_2$ in FIG. 3.

$$2CeO_2 + H_2S \rightarrow Ce_2O_2S + H_2O + 0.5O_2 \quad \text{Equation 4}$$

Figure 4:
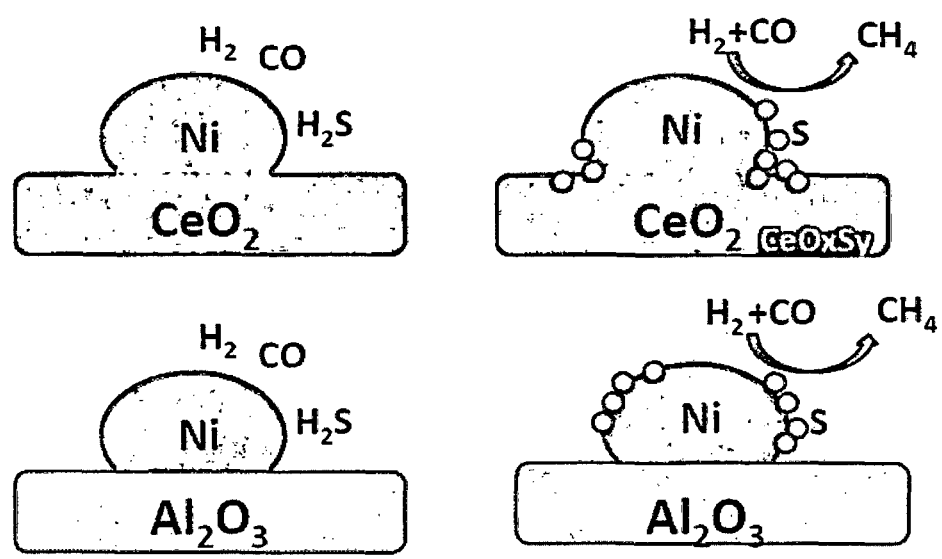
FIG. 4 shows a proposed reaction mechanism of methanation of syngas in the presence of $H_2S$ over Ni/$CeO_2$ (top) and Ni/$Al_2O_3$ (bottom).

A reaction mechanism based on the above experimental results is proposed in FIG. 4. Methanation reaction of syngas is catalysed by Ni. Ni sites are also prone to be poisoned by H$_2$S which decomposes into S+H$_2$. The remaining sulfur is strongly attracted to Ni. NiS is more stable when Ni is supported on Al$_2$O$_3$ since Al$_2$O$_3$ is inert to sulfur. Hence, it is believed that Ni/Al$_2$O$_3$ deactivates quickly when surface Ni is covered by sulfur. However, when Ni is supported on ceria, some oxygen vacancies are generated during the reaction. Hence, some of the sulfur is thought to react/transfer into ceria, and as such the sulfur tolerance of Ni/CeO$_2$ catalysts according to the present invention is enhanced compared to that of Ni/Al$_2$O$_3$.

Interaction of Sulfur with Ni Catalyst Supported on Ce$_{0.9}$Ca$_{0.1}$O$_2$

Figure 5:
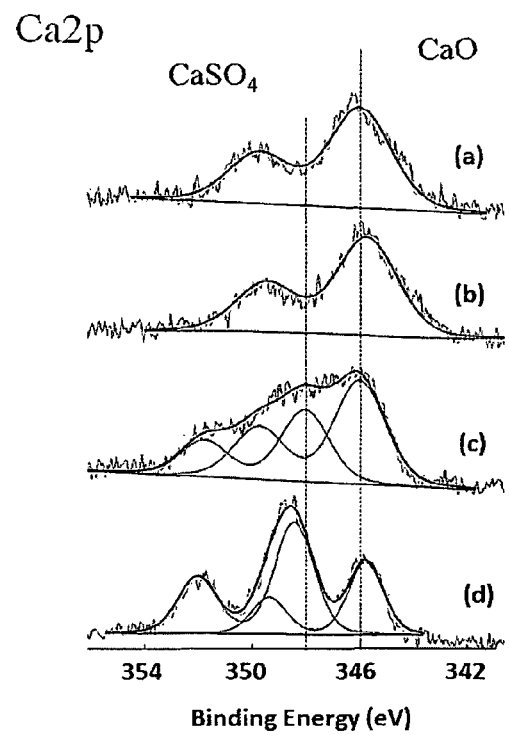
FIG. 5 shows the Ca 2p XPS spectra of (a) as-calcined 5% Ni/$Ce_{0.9}Ca_{0.1}O_2$; (b) spent 5% Ni/$Ce_{0.9}Ca_{0.1}O_2$ after methanation in 20 ppm of $H_2S$ for 5 h; (c) $Ce_{0.9}Ca_{0.1}O_2$ exposed to 100 ppm of $H_2S$ for 16 h at 500° C. and (d) 5% Ni/$Ce_{0.9}Ca_{0.1}O_2$, reduced and exposed to 100 ppm of $H_2S$ for 16 h at 500° C.
Figure 6:
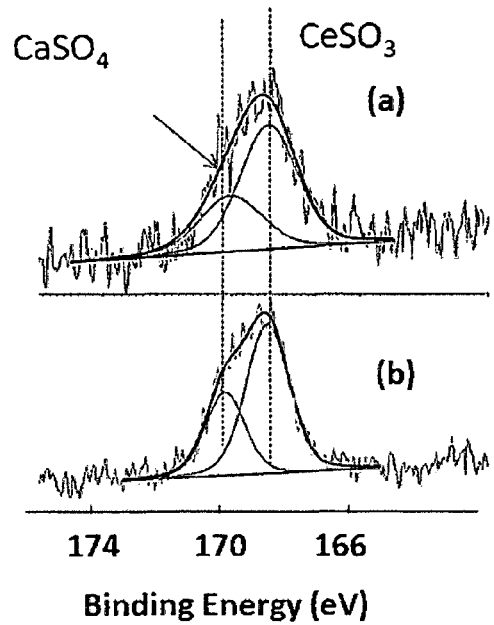
FIG. 6 shows the S 2p XPS spectra of (a) $Ce_{0.9}Ca_{0.1}O_2$ and (b) reduced 5% Ni/$Ce_{0.9}Ca_{0.1}O_2$ exposed to 100 ppm of $H_2S$ for 16 h at 500° C.

XPS analysis was performed to investigate the surface properties of (a) as calcined 5%Ni/Ce$_{0.9}$Ca$_{0.1}$O$_2$; (b) spent 5%Ni/Ce$_{0.9}$Ca$_{0.1}$O$_2$ after methanation in 20 ppm of H$_2$S for 5 h; (c) Ce$_{0.9}$Ca$_{0.1}$O$_2$ exposed to 100 ppm of H$_2$S for 16 h at 500° C. and (d) 5%Ni/Ce$_{0.9}$Ca$_{0.1}$O$_2$, reduced and exposed to 100 ppm of H$_2$S for 16 h at 500° C. FIG. 5 shows the Ca (2p$_{1/2}$, 2p$_{3/2}$) fine structure of these samples. The Ca 2p spectrum of as-calcined 5%Ni/Ce$_{0.9}$Ca$_{0.1}$O$_2$(FIG. 5a)) and spent 5%Ni/Ce$_{0.9}$Ca$_{0.1}$O$_2$(FIG. 5(b)) were similar and the Ca 2p$_{3/2}$ peak at 345.5 eV was characteristic of CaO. These results indicate that the interaction of sulfur with the catalyst support in 20 ppm of H$_2$S for 5 hours may not be detectable by XPS. Therefore, the interaction of sulfur with these catalysts was investigated by sulfurising Ce$_{0.9}$Ca$_{0.1}$O$_2$ and reduced 5%Ni/Ce$_{0.9}$Ca$_{0.1}$O$_2$ in 100 ppm of H$_2$S for 16 h. Two Ca species can be determined through deconvolution of the spectra of Ce$_{0.9}$Ca$_{0.1}$O$_2$ (FIG. 5(c)) and they were assigned to CaO and CaSO$_4$, whose Ca 2p$_{3/2}$ binding energies are at 345.5 eV and 347.9 eV, respectively (B. Demri, D. Muster, *Journal of Materials Processing Technology* 55 (1995) 311-314). In the presence of Ni, two distinct peaks, again corresponding to CaO and CaSO$_4$, were identified (FIG. 5(d)). Moreover, the ratio of CaSO$_4$ to CaO increased with the presence of Ni. This suggests that Ni promotes the formation of CaSO$_4$. From the S 2p XPS spectra in FIG. 6, CeSO$_3$ species can also be found.

The invention claimed is:

1. A method for methanation of a feedstock including carbon monoxide and hydrogen, said method comprising contacting the feedstock with a catalyst, said catalyst comprising a catalytic element selected from the group consisting of Co, Fe, Pt, Ru, Rh, Pd, Ni and Ir disposed on a substrate, wherein said substrate has formula Ce$_{1-x}$M$_x$O$_2$, wherein x is between about 0.01 and about 0.3, and wherein M is a metallic element selected from the group consisting of Y, Gd, Sm and alkaline earth metals.

2. The method of claim 1 wherein the feedstock includes coal gasification effluent and/or biomass gasification effluent.

3. The method of claim 1 wherein the feedstock additionally includes a sulfur-containing gas or vapour.

4. The method of claim 3, comprising a step of depositing the catalytic element on the substrate for reducing poisoning of the catalytic element by the sulfur-containing gas or vapor.

5. The method of claim 4 wherein said depositing is conducted before exposing said catalytic element to the sulfur-containing gas or vapour.

6. The method of claim 4 wherein the depositing is such that the catalytic element is present in discrete regions on the substrate.

7. The method of claim 3 wherein the sulfur-containing gas or vapour includes any one or more of hydrogen sulfide, carbonyl sulfide, sulfur dioxide or an organic thiol.

8. The method of claim 1 wherein the molar ratio of hydrogen to carbon monoxide in the feedstock is between about 4:1 and about 1:1.

9. The method of claim 1 wherein said contacting is conducted at a temperature of between about 250° C. and about 750° C.

10. The method of claim 1 wherein the temperature and feedstock gas hourly space velocity during said contacting are sufficient to achieve equilibrium conversion of carbon oxides to methane.

11. The method of claim 1 wherein the catalytic element is metallic nickel.

12. The method of claim 1 wherein the substrate is particulate.

13. The method of claim 1 wherein x is between about 0.01 and about 0.25.

14. The method of claim 1 wherein the catalyst includes regions of metallic nickel dispersed on a surface of the substrate.

15. The method of claim 1 wherein the catalyst includes between about 1% and about 40% of the catalytic element by weight.

16. The method of claim 1 wherein the substrate has a specific surface area of between about 10 $m^2/g$ and about 300 $m^2/g$.

* * * * *